US00PP19117P2

(12) United States Plant Patent
Luo

(10) Patent No.: US PP19,117 P2
(45) Date of Patent: Aug. 19, 2008

(54) *SCAEVOLA* PLANT NAMED 'SCAX0226'

(50) Latin Name: *Scaevola aemula*
Varietal Denomination: SCAX0226

(75) Inventor: Shuming Luo, Dulwich Hill (AU)

(73) Assignee: Amerinova Properties LLC, Bonsall, CA (US)

( * ) Notice: Subject to any disclaimer, the term of this patent is extended or adjusted under 35 U.S.C. 154(b) by 0 days.

(21) Appl. No.: 11/800,768

(22) Filed: May 7, 2007

(51) Int. Cl.
*A01H 5/00* (2006.01)

(52) U.S. Cl. ..... Plt./363
(58) Field of Classification Search ..... Plt./363
See application file for complete search history.

*Primary Examiner*—Annette H. Para
(74) *Attorney, Agent, or Firm*—C. A. Whealy

(57) ABSTRACT

A new and distinct cultivar of *Scaevola* plant named 'SCAX0226', characterized by its compact, mounded and outwardly spreading plant habit; freely branching habit; freely flowering habit; and violet-colored flowers.

1 Drawing Sheet

Botanical designation: *Scaevola aemula.*
Cultivar denomination: 'SCAX0226'.

BACKGROUND OF THE INVENTION

The present invention relates to a new and distinct cultivar of *Scaevola,* botanically known as *Scaevola aemula,* and hereinafter referred to by the name 'SCAX0226'.

The new *Scaevola* is a product of a planned breeding program conducted by the Inventor in Cobbitty, New South Wales, Australia. The objective of the breeding program is to create new freely-flowering *Scaevola* cultivars with attractive flower color.

The new *Scaevola* originated from a cross-pollination made by the Inventor in Cobbitty, New South Wales, Australia in October, 2001, of a proprietary selection of *Scaevola aemula* identified as code number 01.1.1, not patented, as the female, or seed, parent with a proprietary selection of *Scaevola aemula* identified as code number 01.1.2, not patented, as the male, or pollen, parent. The cultivar SCAX0226 was discovered and selected by the Inventor as a flowering plant within the progeny of the stated cross-pollination in a controlled environment in Cobbitty, New South Wales, Australia in October, 2002.

Asexual reproduction of the new *Scaevola* by terminal cuttings in a controlled environment in Cobbitty, New South Wales, Australia since October, 2002, has shown that the unique features of this new *Scaevola* are stable and reproduced true to type in successive generations.

SUMMARY OF THE INVENTION

The cultivar SCAX0226 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'SCAX0226'. These characteristics in combination distinguish 'SCAX0226' as a new and distinct cultivar of *Scaevola:*

1. Compact, mounded and outwardly spreading plant habit.

2. Freely branching habit.
3. Freely flowering habit.
4. Violet-colored flowers.

Plants of the new *Scaevola* can be compared to plants of the female parent selection. Plants of the new *Scaevola* differ from plants of the female parent selection in the following characteristics:

1. Plants of the new *Scaevola* are more compact than plants of the female parent selection.
2. Plants of the new *Scaevola* have smaller leaves than plants of the female parent selection.
3. Plants of the new *Scaevola* have violet-colored flowers whereas plants of the female parent selection have purple-colored flowers.

Plants of the new *Scaevola* can be compared to plants of the male parent selection. Plants of the new *Scaevola* differ from plants of the male parent selection in the following characteristics:

1. Plants of the new *Scaevola* are more compact than and not as trialing as plants of the male parent selection.
2. Plants of the new *Scaevola* have larger leaves than plants of the male parent selection.

Plants of the new *Scaevola* can be compared to plants of the *Scaevola aemula* cultivar Newon, disclosed in U.S. Plant Pat. No. 10,584. In side-by-side comparisons conducted in Cobbitty, New South Wales, Australia, plants of the new *Scaevola* differed from plants of the cultivar Newon in the following characteristics:

1. Plants of the new *Scaevola* were more compact than plants of the cultivar Newon.
2. Plants of the new *Scaevola* had smaller leaves than plants of the cultivar Newon.
3. Flowers of plants of the new *Scaevola* and the cultivar Newon differed in flower color as plants of the cultivar Newon had purple-colored flowers.

BRIEF DESCRIPTION OF THE PHOTOGRAPHS

The accompanying colored photographs illustrate the overall appearance of the new *Scaevola,* showing the colors as true as it is reasonably possible to obtain in colored reproductions of this type. Colors in the photographs may differ slightly from the color values cited in the detailed botanical description which accurately describe the colors of the new *Scaevola*.

The photograph at the bottom of the sheet comprises a side perspective view of a typical flowering plant of 'SCAX0226' grown in a container.

The photograph at the top of the sheet comprises a close-up view of typical flowers of 'SCAX0226'.

DETAILED BOTANICAL DESCRIPTION

The photographs and following observations, measurements and values describe plants grown in Bonsall, Calif. in one-gallon containers in an outdoor nursery during the summer under conditions which closely approximate commercial production. During the production of the plants, day temperatures ranged from about 18° C. to 38° C. and night temperatures ranged from about 16° C. to 24° C. Plants were about seven weeks old when the photographs and the description were taken. In the description, color references are made to The Royal Horticultural Society Colour Chart, 1995 Edition, except where general terms of ordinary dictionary significance are used.

Botanical classification: *Scaevola aemula* cultivar SCAX0226.

Parentage:

*Female, or seed, parent.*—Proprietary selection of *Scaevola aemula* identified as code number 01.1.1, not patented.

*Male or pollen parent.*—Proprietary selection of *Scaevola aemula* identified as code number 01.1.2, not patented.

Propagation:

*Type.*—By terminal cuttings.

*Time to initiate roots.*—About one to two weeks.

*Time to develop roots.*—About two to three weeks.

*Root description.*—Fibrous; white in color.

*Rooting habit.*—Moderate branching; moderately dense.

Plant description:

*Plant form and growth habit.*—Compact, mounded and outwardly spreading plant habit. Vigorous growth habit.

*Branching habit.*—Freely branching, usually about seven lateral branches each with about three to four secondary lateral branches.

*Plant height.*—About 20 cm.

*Plant diameter* (*area of spread*).—About 46 cm.

Lateral branch description:

*Length.*—About 29 cm.

*Diameter.*—About 3 mm.

*Internode length.*—About 1.5 cm.

*Texture.*—Pubescent.

*Color.*—144A.

Foliage description:

*Arrangement.*—Alternate, simple.

*Length.*—About 3.8 cm.

*Width.*—About 1.8 cm.

*Shape.*—Oblanceolate to spatulate.

*Apex.*—Broadly acute.

*Base.*—Attenuate.

*Margin.*—Irregular serrations.

*Texture, upper and lower surfaces.*—Pubescent; coarse.

*Venation pattern.*—Pinnate, arcuate.

*Color.*—Developing foliage, upper surface: 137A. Developing foliage, lower surface: 137B. Fully developed foliage, upper surface: 137A; venation, 137B. Fully developed foliage, lower surface: 137C; venation, 147B.

*Petiole.*—Length: About 2 cm. Diameter: About 3 mm. Texture, upper and lower surfaces: Pubescent. Color, upper and lower surfaces: 144A.

Flower description:

*Flower type and shape.*—Zygomorphic, semi-circular, fan-shaped flowers with five petals fused at the base to form a tubular flower throat. Flower throat open along the upper surface exposing reproductive organs. Flowers not fragrant.

*Flower arrangement and quantity.*—Solitary sessile flowers arise from leaf axils. Flowers face mostly outwardly. Freely flowering habit, typically about ten to twelve open flowers and about 18 flower buds per lateral branch.

*Flowering time.*—Plants flower continuously from May through September in Southern California. Flowers typically last about five to seven days on the plant. Flowers not persistent.

*Flower buds.*—Shape: Oblanceolate. Length: About 2.1 cm. Diameter: About 6 mm. Color: 92B; central stripes, 145B.

*Flowers.*—Length, fan: About 1.2 cm. Width, fan: About 2.5 cm. Flower throat diameter: About 5 mm. Flower tube length: About 2.2 cm. Flower tube diameter, base: About 2.5 mm.

*Petals.*—Quantity: Five, fused at base. Shape: Elliptic. Apex: Acuminate. Margin: Entire. Length, above tube: About 1.3 cm. Width, above tube: About 4 mm. Texture, upper surface: Lobes, smooth; flower throat, whiskered. Texture, lower surface: Pubescent. Color: When opening, upper surface: 90C. When opening, lower surface: 91A; center stripe, 148B. Fully opened, upper surface: 90B; towards the throat, 145D; throat, 145A. Lobe apices becoming closer to 91B with development. Fully opened, lower surface: 91A; center stripes, 91C to 91D; at the base of the tube, 145A. Color becoming closer to 91B to 91C with development.

*Sepals.*—Quantity and arrangement: Five in a single whorl. Length: About 8 mm. Width: About 2 mm. Shape: Lanceolate. Apex: Acute. Base: Attenuate, clasping. Margin: Entire. Texture, upper and lower surfaces: Pubescent. Color, upper and lower surfaces: 145C.

*Reproductive organs.*—Androecium: Stamen quantity per flower: About five. Filament length: About 2 mm. Filament color: 145B. Anther shape: Narrowly oblong. Anther length: About 1 mm. Anther color: 160B. Pollen: Scarce. Pollen color: 160B. Gynoecium: Pistil quantity per flower: One. Pistil length: About 1.2 cm. Style length: About 8 mm. Style color: 79C. Stigma shape: Triangular. Stigma color: 145D. Ovary color: 145A.

*Seed/fruit.*—Seed and fruit production has not been observed.

Temperature tolerance: Plants of the new *Scaevola* have been observed to tolerate temperatures from about 10° C. to about 40° C.

Pathogen/pest resistance: Plants of the new *Scaevola* have not been shown to be resistant to pathogens and pests common to *Scaevola*.

It is claimed:

1. A new and distinct *Scaevola* plant named 'SCAX0226' as illustrated and described.

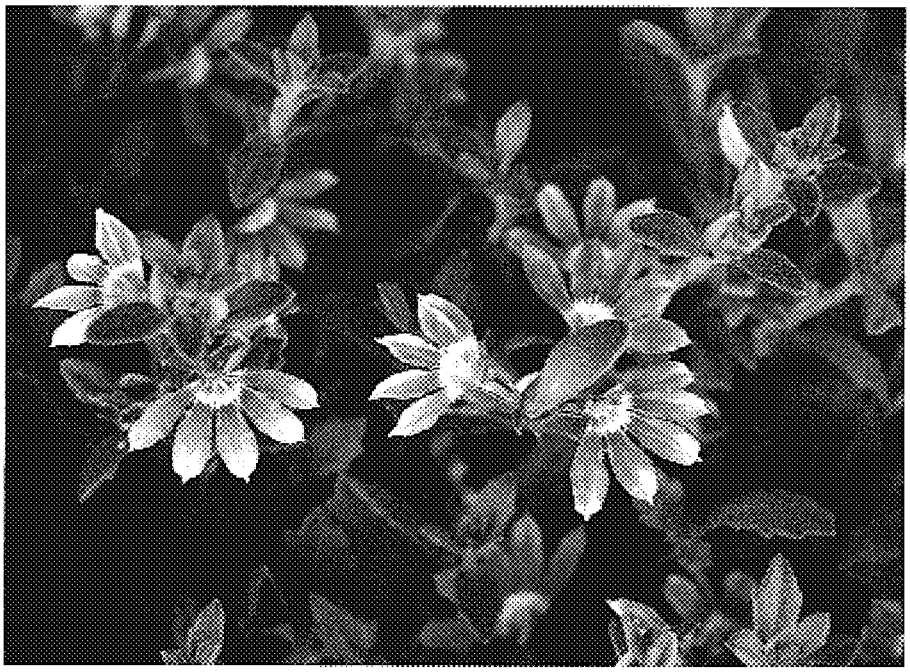
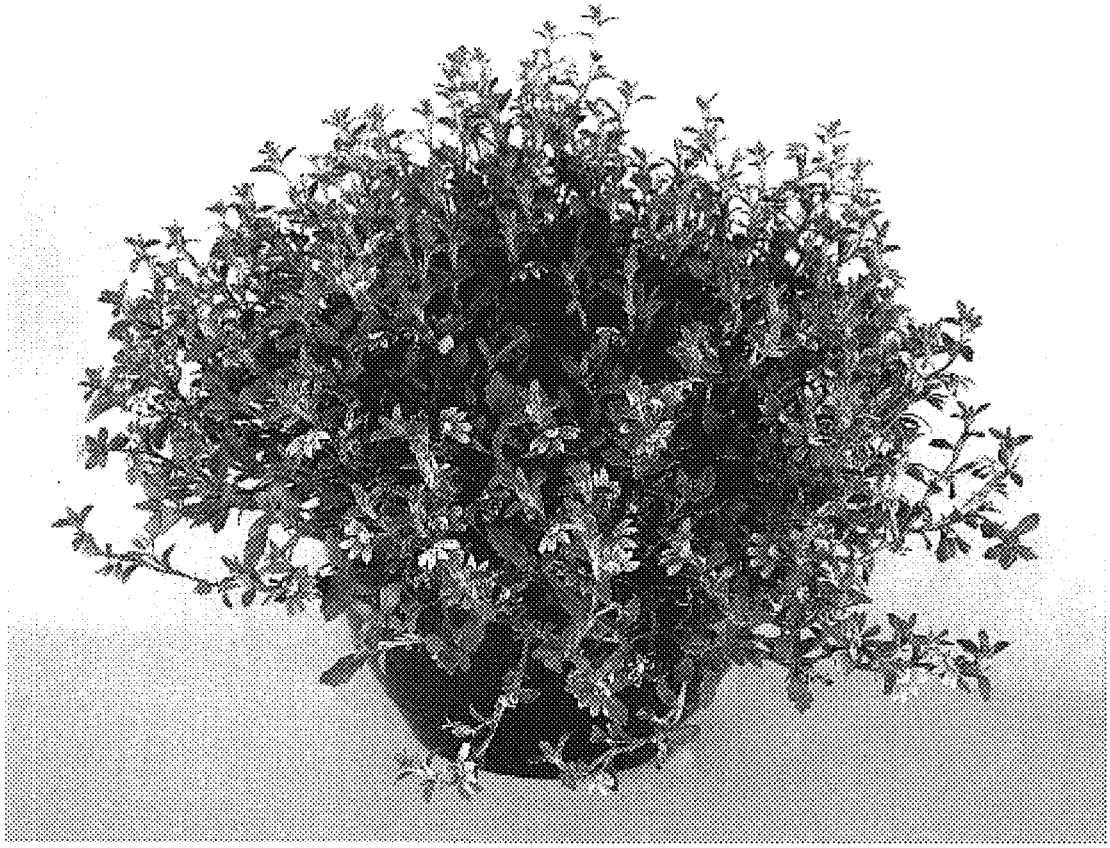

* * * * *